(12) United States Patent
Lohoff

(10) Patent No.: US 8,821,149 B2
(45) Date of Patent: Sep. 2, 2014

(54) WEB TREATMENT APPARATUS HAVING CENTER BEARER RING

(75) Inventor: Michael Lee Lohoff, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 609 days.

(21) Appl. No.: 13/101,712

(22) Filed: May 5, 2011

(65) Prior Publication Data

US 2012/0283681 A1 Nov. 8, 2012

(51) Int. Cl.
*B29C 59/04* (2006.01)
(52) U.S. Cl.
USPC ............................................. 425/363; 425/367
(58) Field of Classification Search
USPC .................................................. 425/363, 367
See application file for complete search history.

(56) References Cited

U.S. PATENT DOCUMENTS

| | | | | | |
|---|---|---|---|---|---|
| 1,566,771 | A | * | 12/1925 | Perky | 425/363 |
| 2,752,632 | A | * | 7/1956 | Winstead | 425/363 |
| 3,796,423 | A | * | 3/1974 | Shuster | 100/176 |
| 4,155,693 | A | * | 5/1979 | Raley | 425/363 |
| 4,171,655 | A | | 10/1979 | Voorhees | |
| 4,220,083 | A | | 9/1980 | Fischer | |
| 4,234,300 | A | * | 11/1980 | Yamagisi et al. | 425/363 |
| 4,793,229 | A | | 12/1988 | Kleber | |
| 4,938,677 | A | * | 7/1990 | Robbins, III | 425/363 |
| 5,770,122 | A | * | 6/1998 | Curchod | 425/363 |
| 6,311,615 | B1 | | 11/2001 | Hilliard | |
| 7,146,893 | B2 | | 12/2006 | Aichele | |
| 7,922,473 | B2 | | 4/2011 | Gelli et al. | |
| 2002/0022108 | A1 | * | 2/2002 | Krantz et al. | 425/363 |
| 2003/0183053 | A1 | | 10/2003 | Amend et al. | |
| 2004/0051948 | A1 | * | 3/2004 | Reed | 425/363 |
| 2004/0188874 | A1 | * | 9/2004 | Hikita et al. | 425/363 |
| 2008/0066632 | A1 | | 3/2008 | Raueiser | |
| 2010/0030176 | A1 | | 2/2010 | Beckert et al. | |
| 2010/0035740 | A1 | | 2/2010 | Yamamoto | |
| 2010/0163161 | A1 | | 7/2010 | Gilgenbach et al. | |
| 2010/0168705 | A1 | | 7/2010 | Stabelfeldt et al. | |
| 2010/0201024 | A1 | | 8/2010 | Gibson et al. | |
| 2010/0267536 | A1 | | 10/2010 | Ruoff | |

FOREIGN PATENT DOCUMENTS

| | | |
|---|---|---|
| EP | 1186387 A2 | 8/2001 |
| EP | 1925408 B1 | 11/2007 |
| WO | 2006004474 A1 | 12/2006 |
| WO | 2009127399 A1 | 10/2009 |

OTHER PUBLICATIONS

International Search Report and Written Opinion for PCT/IB2012/051437 dated Nov. 23, 2012; 11 pages.

* cited by examiner

*Primary Examiner* — James Mackey
(74) *Attorney, Agent, or Firm* — Armstrong Teasdale LLP

(57) ABSTRACT

Apparatus for treating at least one web passing through the apparatus includes a first roller and a second roller positioned adjacent the first roller to define a nip for receiving the at least one web. The first roller has a pair of spaced apart ends, a length extending between the ends, a circumference, and at least one bearer ring extending around the circumference of the first roller generally at a center of the first roller.

20 Claims, 8 Drawing Sheets

WEB TREATMENT APPARATUS HAVING CENTER BEARER RING

FIELD

The field of the invention relates generally to web treatment apparatus and more specifically to web treatment apparatus having a center bearer ring and a method of using the apparatus.

BACKGROUND

Some people rely on disposable absorbent products in their everyday lives including, for example, disposable absorbent articles such as adult incontinence products, enuresis pants, training pants, and diapers. Many manufacturers of these absorbent articles seek to better meet the needs of users. For example, there is an ongoing need to improve fit, discretion, and leakage protection for many of these articles.

Some absorbent articles employ elasticization across the front and/or back of the article to keep the article snug against the wearer during use. Some of these articles employ a multiplicity of elastic strands within front and/or back waist panels of the article to provide the elasticization, while others employ elastomeric polymeric films, which are often sandwiched with one or more nonwoven layers.

Most absorbent articles include an absorbent member, constructed from wood pulp fluff, superabsorbent polymers, and/or other absorbent material to absorb fluids (e.g., urine) discharged by the user. The absorbent member is typically positioned in the crotch region of the article and extends forward and backward into the article's front and/or back regions. In some absorbent articles, the elastic members that extend across the front and/or back waist panels of the article overlap the absorbent member at various locations since the absorbent member extends forward/backward into the front/back waist regions of the article. Often, the tension of the elastic members tends to gather the absorbent member, or cause it to "bunch". Such bunching of the absorbent member can create fit and discretion problems.

For example, an absorbent article that is bunched in its front and/or back waist region is less likely to fit snug against the body of the user during wear. As a result, the potential of the article leaking is significantly increased. Bunching also tends to make the article more bulky and therefore more visible under clothing thereby decreasing the article's discretion. These results are particularly problematic for incontinence articles, such as enuresis pants and adult pull-on style disposable absorbent underwear, as the wearers of these articles generally are embarrassed about their condition and wish to employ protection which is as discreet as possible.

To inhibit bunching of the absorbent member in some absorbent articles, the elasticization across the front and/or back of the article is at least partially deadened (i.e., rendered substantially non-elastomeric). Often times, however, the apparatus and processes used to deaden the elasticization result in the deadened areas being non-uniform. That is, the resulting deadened portions of the front and/or back of the articles have varying amounts of elasticization. Moreover, known apparatus for deadening the front and/or back regions of articles often limit the width of the web that can be deadened.

Thus, there remains a need for apparatus and processes of manufacturing articles that can provide for webs having greater widths and that result in a more uniform deadened portion.

SUMMARY

In one aspect, apparatus for treating at least one web passing through the apparatus generally comprises a first roller and a second roller. The first roller has a pair of spaced apart ends, a length extending between the ends, a circumference, and at least one bearer ring extending around the circumference of the first roller generally at a center of the first roller. The second roller is positioned adjacent the first roller to define a nip for receiving the at least one web.

In another aspect, apparatus for treating at least one web generally comprises a first roller and a second roller. The first roller has a pair of spaced apart ends, a length extending between the ends, a circumference, and at least one bearer ring extending around the circumference of the first roller, the at least one bearer ring being disposed between and spaced from the ends of the first roller. The second roller is positioned adjacent the first roller to define a nip for receiving the at least one web.

In still another aspect, a method of treating a web generally comprises directing a web toward an apparatus for treating the web. The apparatus comprises a first roller and a second roller arranged relative to the first roller to define a nip for receiving the web. The first roller of the apparatus is rotated in a first direction. The first roller includes two ends, a length extending between the two ends, at least one raised area adapted to treat the web, and at least one bearer ring. The at least one bearer ring extends around the circumference of the first roller and is disposed at a location between and spaced from the ends of the first roller. The second roller of the apparatus is rotated in a second direction. The second direction is opposite to the first direction. The web is fed to the nip of the apparatus such that the web is contacted by the raised area on the first roller to treat the web.

BRIEF DESCRIPTION OF THE DRAWINGS

Corresponding reference characters indicate corresponding parts throughout the drawings.

DETAILED DESCRIPTION OF THE DRAWINGS

Figure 1:
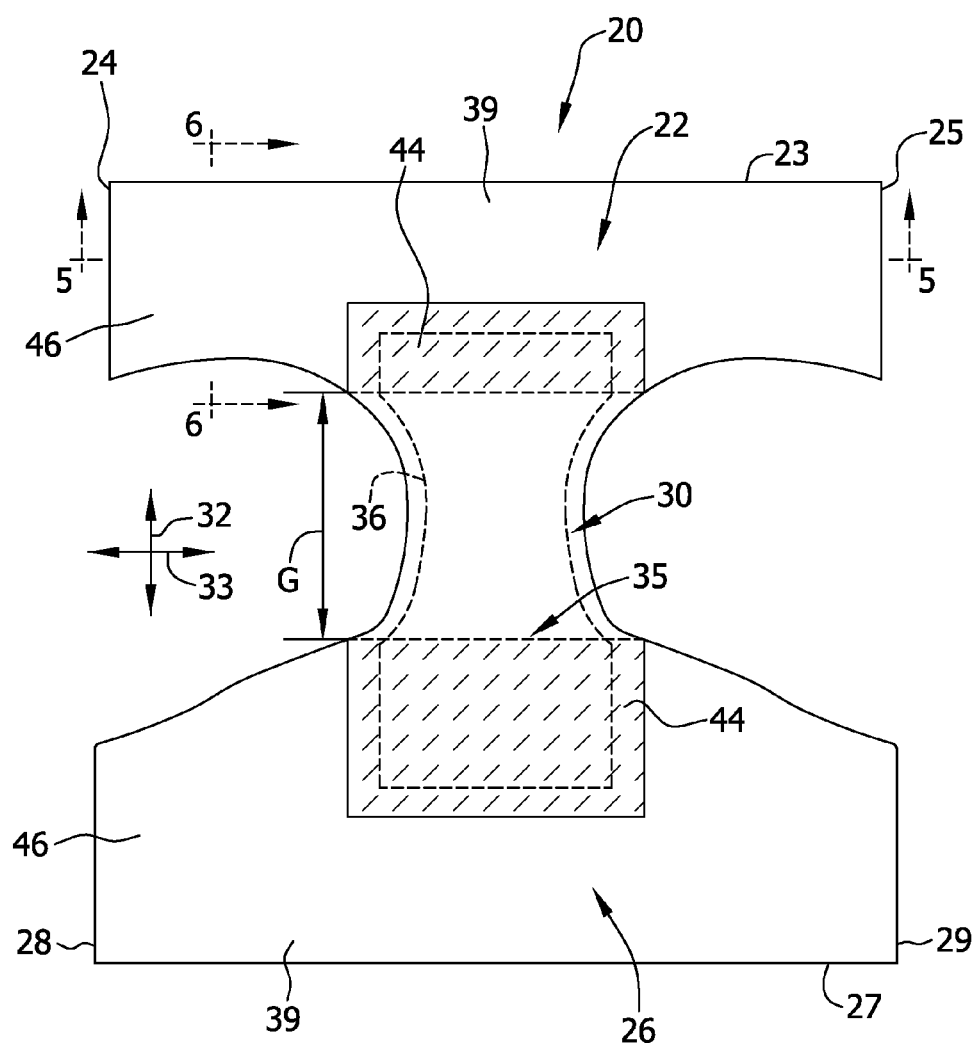
FIG. 1 is plan view of one embodiment of an absorbent article, the article being in a longitudinally stretched and laid-flat condition showing a surface of the article that faces the wearer during wear.
Figure 2:
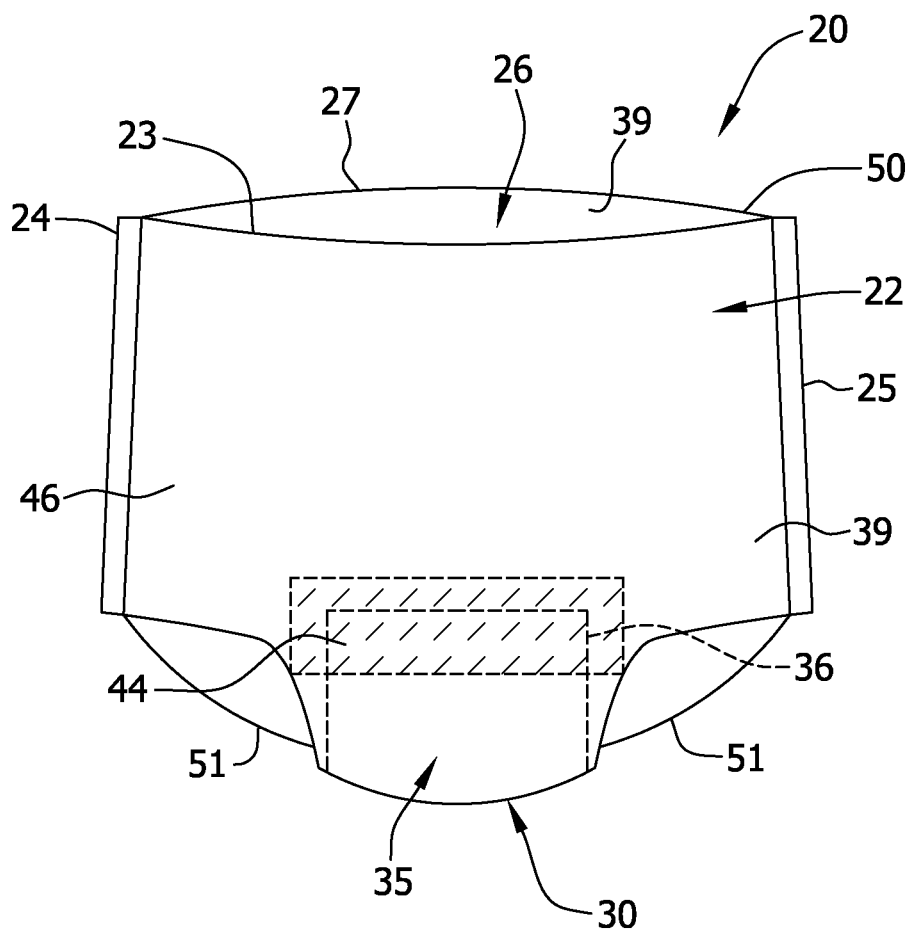
FIG. 2 is a front view of the absorbent article of FIG. 1 with front and back waist regions of the article joined such that the garment is in a pull-on, pant-like configuration.

FIGS. 1 and 2 illustrate one suitable embodiment of an absorbent article, indicated generally at 20. The absorbent article 20 has a front region 22, a back region 26, and a crotch region 30 disposed longitudinally between and interconnecting the front and back regions. The front, back and crotch regions 22, 26, 30 are indicated generally by the respective reference number. In the front region 22, the absorbent article 20 has a front edge 23 and transversely opposed first and second front side edges 24, 25. A back edge 27 and transversely opposed first and second back side edges 28, 29 are located in the back region 26 of the absorbent article 20. As illustrated in FIG. 1, the absorbent article 20 defines a longitudinal direction 32 and a transverse direction 33, which is perpendicular to the longitudinal direction.

Figure 3:
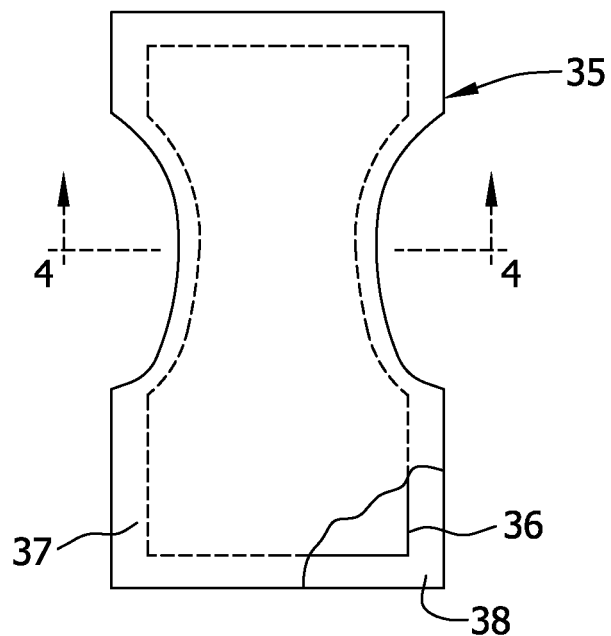
FIG. 3 is a plan view of an absorbent insert suitable for use with the absorbent article of FIGS. 1 and 2, a portion of the insert being cut away to show underlying features.
Figure 4:
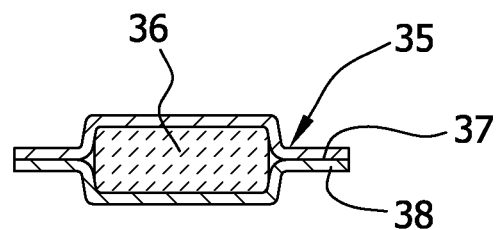
FIG. 4 is a cross-section taken along line 4-4 of FIG. 3.

The absorbent article 20 includes an absorbent insert, indicated generally at 35, that extends longitudinally from the front region 22 through the crotch region 30 to the back region 26. With reference now to FIGS. 3 and 4, the illustrated absorbent insert 35 includes an absorbent member 36 disposed between a liquid permeable liner 37 and a liquid impermeable backsheet 38. The absorbent member 36 can be constructed of materials suitable for absorbing liquid excretions, such as wood pulp fluff, superabsorbent polymers, absorbent foam, and the like. The absorbent member 36 can be encased in one or more substrates. For example, the absorbent member 36 can be wrapped in a tissue and/or a nonwoven substrate.

With reference again to FIGS. 1 and 2, the front and back regions 22, 26 of the illustrated absorbent article 20 are constructed of discrete pieces of laminate 39 that are connected via the absorbent insert 35. That is, the front region 22 is formed by a piece of laminate 39 and the back region 26 is formed by a separate piece of laminate. As seen in FIG. 1, the laminate 39 forming the front region 22 is spaced from the laminate forming the back region 26 to define a gap G. The absorbent insert 35 spans the gap G and connects the laminate 39 forming the front region 22 to the laminate forming the back region 26.

Figure 5:
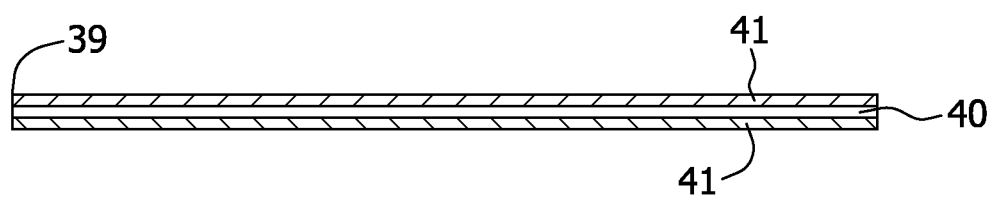
FIG. 5 is a cross-section taken along line 5-5 of FIG. 1.
Figure 6:
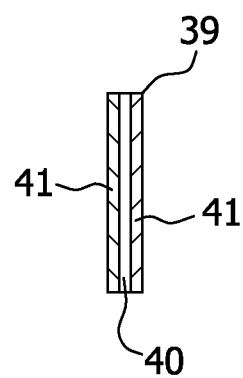
FIG. 6 is a cross-sectional taken along line 6-6 of FIG. 1.

In one suitable embodiment, the laminate 39 used to form both the front and back regions 22, 26 of the absorbent article 20 comprises a polymeric film layer 40 and at least one nonwoven layer 41 (FIGS. 5 and 6). In the illustrated embodiment, for example, the laminate 39 has two nonwoven layers 41 superposed on opposing top and bottom surfaces of the polymeric film 40 such that the polymeric film is sandwiched between the two nonwoven layers. The polymeric film 40 and both nonwoven layers 41 extend substantially throughout the entire area of the laminate 39. While the laminate 39 used to form the front and back regions 22, 26 is the same in the illustrated absorbent article 20, it is contemplated that the laminate used to form the front region 22 can be different than the laminate used to form the back region 26.

As seen in FIG. 1, a portion of the absorbent insert 35 overlaps a portion of the laminate 39 in the front and back regions 22, 26 to define overlapped regions 44 and non-overlapped regions 46. In one suitable embodiment, at least a portion of each of the overlapped regions 44 of the laminate 39 is non-elastomeric, and at least a portion of the non-overlapped region 46 of the laminate 39 is elastomeric. The overlapped regions 44 are indicated in FIGS. 1 and 2 by a pattern of diagonally extending dashes.

In one suitable embodiment, the entire laminate 39 forming the front and back regions 22, 26 is constructed of an elastomeric film laminate having portions (e.g., the portions generally corresponding to the overlapped regions 44) thereof "deactivated" or "deadened" to render it non-elastomeric. As used herein, "elastomeric" refers to a material or composite that can be elongated by at least 50 percent of its relaxed length and that will recover, upon release of the applied force, at least 50 percent of its elongation. It is generally preferred that the elastomeric material or composite be capable of being elongated by at least 100 percent, more preferably by at least 200 percent, of its relaxed length and recover, upon release of an applied force, at least 50 percent of its elongation. "Non-elastomeric" refers to a material or composite that is non-extensible, or that is extensible but will recover no more than 20 percent of its elongated length after release of an applied elongating force. "Non-extensible" refers to a material that cannot stretch or extend by more than 25 percent of its relaxed length without fracture upon application of a biasing force. "Partially elastomeric" refers to a material or composite which can be elongated by at least 50 percent of its relaxed length and which will recover, upon release of the applied force, more than 20 percent but less than 50 percent of its elongation.

It should be noted that in analyzing the laminate 39 or regions thereof for extensible or elastic character, the laminate is to be examined removed from separately attached components. For example, before examining the extensible or elastic properties of the overlapped regions 44 of the laminates 39, the absorbent insert 35 should be removed. That is, the absorbent insert 35, which comprises the absorbent member 36 sandwiched between the liner 37 and the backsheet 38, should be peeled away from the laminates 39 prior to examining extensibility or elasticity of any portion of the laminates.

In one suitable embodiment, the majority of the overlapped region 44 of each of the laminates 39 is non-elastomeric. That is, more than 50 percent of the area of the overlapped region 44 of the laminates 39 is non-elastomeric. In one suitable embodiment, more than 75 percent, and in still a more suitable embodiment more than 90 percent of the area of the overlapped region 44 of the laminates 39 is non-elastomeric. In another suitable embodiment, the entire overlapped region 44 of the laminates 39 (i.e., 100 percent) is non-elastomeric. For example, in the absorbent article 20 illustrated in FIGS. 1 and 2, the entire overlapped region 44 of the laminates 39 is non-elastomeric and generally the same size and shape as the portion of the absorbent insert 35 that overlaps it.

In other suitable embodiments, the portion of the laminates 35 rendered non-elastomeric can be larger than the corresponding overlapped region 44. For example, the non-elastomeric area of the laminates 39 can be 125 percent or less larger, more preferably 120 percent or less larger, and still more preferably 110 percent or less larger in area than the overlapped region 44. By having the non-elastomeric region of the laminates 39 larger than the area of the overlapped regions 44, it is possible to accommodate the process registration variability common in typically high-speed absorbent article manufacturing processes. In other words, the footprint of the non-elastomeric region of the laminates 39 being larger relative to the footprint of the absorbent insert 35 in the front and back regions 22, 26 of the absorbent article 20 allows for variability in registration as the absorbent insert is mated to the laminates. Furthermore, in such embodiments, the relatively larger non-elastomeric region (larger relative to the overlapped region 44) will aid in minimizing the amount of bunching directly around the periphery of the absorbent insert 35, which can provide a smoother, "flatter", more underwear-like garment.

As seen in FIGS. 2, the first front side edge 24 can be connected to the first back side edge 28, and the second front side edge 25 can be connected to the second back side edge 29 to define a pull-on, pant-like configuration of the absorbent article 20 having a waist opening 50 and two leg openings 51. FIG. 2 illustrates the side edges 24, 25, 28, 29 of the absorbent article 20 being joined together with non-refastenable butt seams. The first and second back side edges 28, 29 are illustrated in FIG. 1. It is understood, however, the side edges 24, 25, 28, 29 can be joined together at refastenable seams and/or at seams other than butt seams (e.g., overlapping seams).

Figure 7:
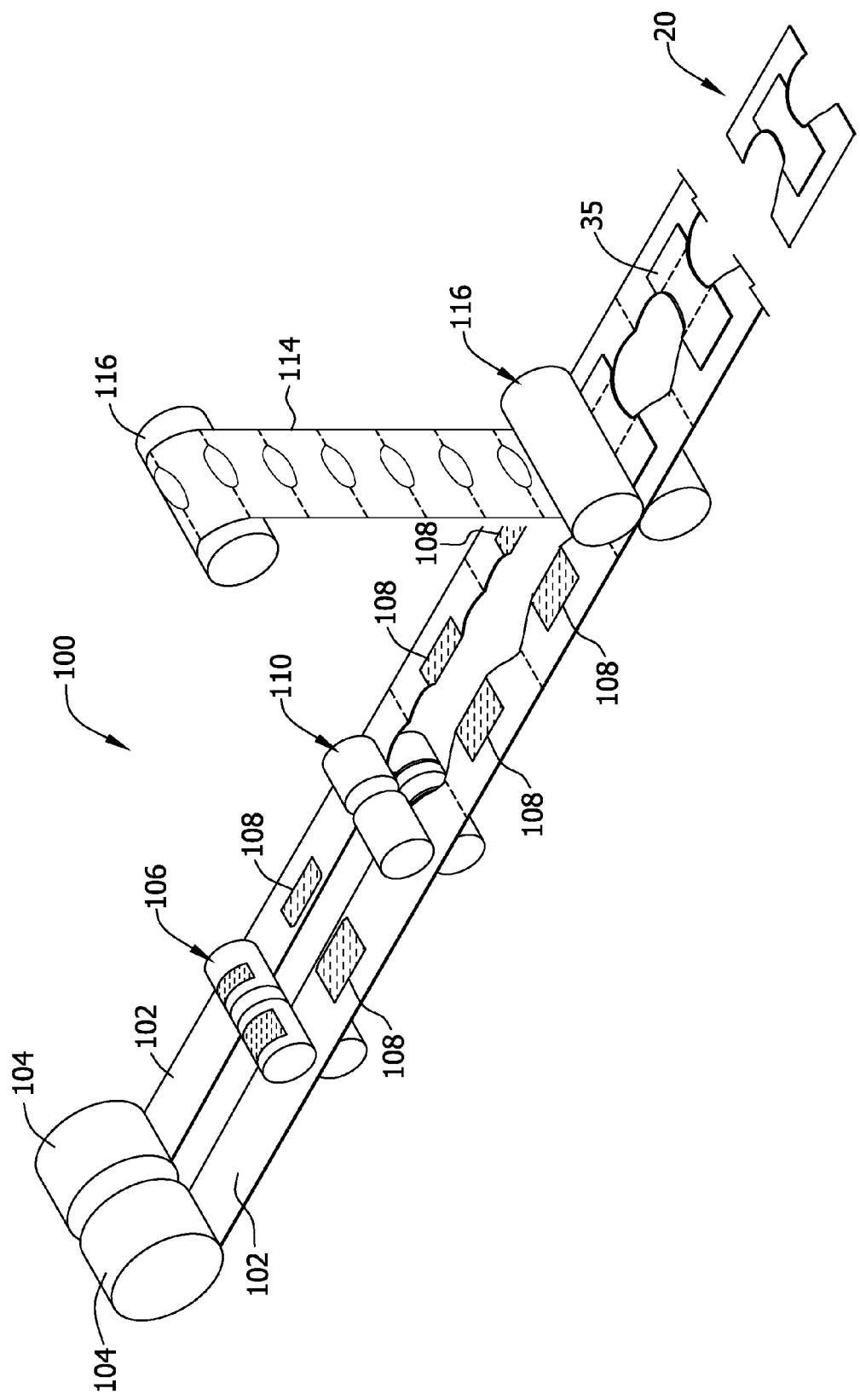
FIG. 7 illustrates one embodiment of a manufacturing process for manufacturing the absorbent article illustrated in FIGS. 1-6.

FIG. 7 schematically illustrates a portion of one embodiment of a process 100 suitable for making a plurality of the absorbent article 20 illustrated in FIGS. 1-6. As seen in FIG. 7, two continuous supplies of elastomeric laminate web 102 used to form the front and back regions 22, 26 of the absorbent article 20 are provided from suitable supply sources 104. That is, one of the supply rolls 104 supplies web 102 to form the front region 22 of the absorbent article 20 and the other supply roll supplies web to form the back region 26. While two supply sources 104 are illustrated in FIG. 7, it is understood that a single supply source can be used. In such an embodiment, the web 102 can be cut generally along its longitudinal centerline to form two discrete webs.

Each of the webs 102 is fed to a web treatment apparatus, indicated generally at 106, to treat (e.g., "deaden") a portion 108 of the web. More specifically, each of the webs 102 is fed to the web treatment apparatus 106 in a stretched, elongated state wherein the treatment apparatus renders the acted on portion 108 of each of the elastomeric laminate webs generally non-elastomeric. The web treatment apparatus 106 and its operation are described in detail below.

In the illustrated embodiment, each of the elastomeric laminates webs 102 are then trimmed at a cutting station, indicated generally at 110. The trimmed portions of each of the webs 102 will define the leg openings 51 of the absorbent article. It is contemplated that the webs 102 can pass through the cutting station 110 before passing through the web treatment apparatus 106.

After portions of each of the laminate webs 102 are deadened and cut, a web 114 of absorbent inserts 35 are supplied from a suitable supply source 116. The supply source 116 can be any conventional mechanism for supplying the web 114 of absorbent inserts 35. The web 114 of absorbent inserts 35 is cut at a cutting/bonding station, indicated generally at 116, to form a plurality of discrete absorbent inserts. As seen in FIG. 7, each of the absorbent inserts 35, which are non-stretchable, are oriented generally in the cross-machine direction with respect to the webs 102 and bonded to each the webs, which are traveling in the machine direction, at the cutting/bonding station 116. The absorbent inserts 35 can be bonded to the webs 102 using any suitable bonding technique. For example, the absorbent inserts 35 can be bonded to the webs 102 using any suitable bonded technique including pressure, adhesive, thermal and/or ultrasonic bonding.

In one suitable embodiment, the absorbent inserts 35 are generally aligned with and bonded to the deadened portions 108 of the webs 102 such that the absorbent insert at least partially overlies the deadened portion. As explained above, the deadened portions 108 of the absorbent articles 20 can have an area greater than, less than, or generally equal to the area of the absorbent insert overlying it.

After the absorbent inserts 35 are bonded to the webs 102, a cutter (not shown) selectively cuts the webs to form discrete absorbent articles 20. Such cutters are generally known to those skilled in the art and can include, for example, the combination of a cutting roll and an anvil roll through which the web travels. Cutting of the stretched webs 102 causes them to retract except for the portions 108 that were deadened by the treatment apparatus 106. As a result, bunching of the absorbent insert 35 caused by the webs 102 retracting is inhibited.

The discrete absorbent articles 20 can then be folded at a folding station (now shown) using a suitable folding mechanism (e.g., blade folders, linear folders, book folders, tucker blades). In one suitable configuration, the absorbent articles 20 are folded about a fold line generally bisecting the absorbent articles. As such, the front and back regions 22, 26 of each absorbent articles 20 are positioned in facing relationship. The resulting fold line extends generally about the transverse axis 33 of the absorbent articles through the crotch region 30, which is defined by the absorbent insert 35.

Once the absorbent articles 20 are folded, they can be stacked, such as by a suitable stacking apparatus, and packaged. Other suitable absorbent articles and methods of manufacturing the articles are described in U.S. patent application Ser. No. 12/346,060 entitled Disposable Absorbent Garments Employing Elastomeric Film Laminates with Deactivated Regions and U.S. patent application Ser. No. 12/346,136 entitled Process for Making Disposable Absorbent Garments Employing Elastomeric Film Laminates with Deactivated Regions. Both of these patent applications are incorporated herein in their entireties.

Figure 8:
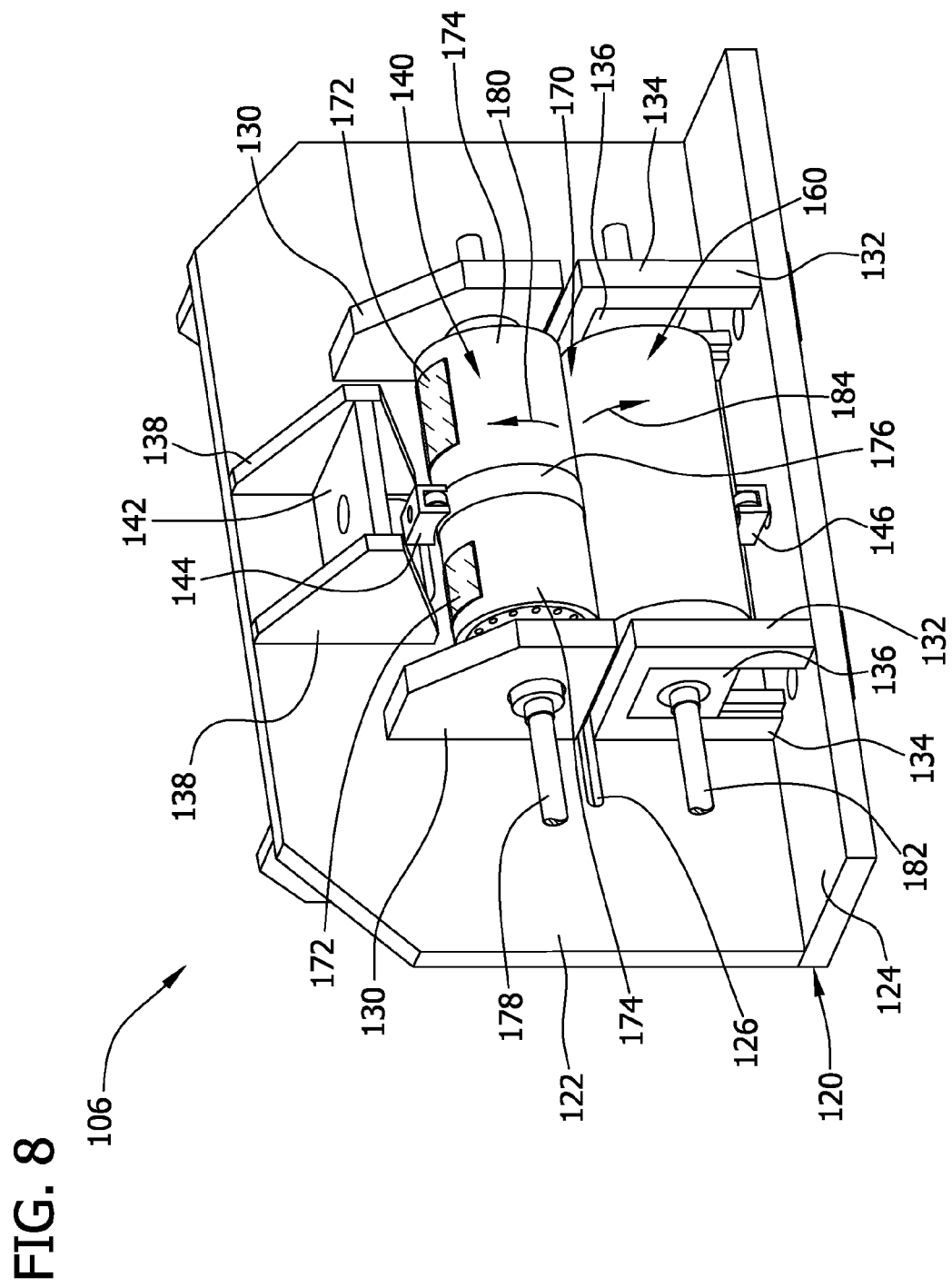
FIG. 8 is a perspective view of one embodiment of a web treatment apparatus.
Figure 9:
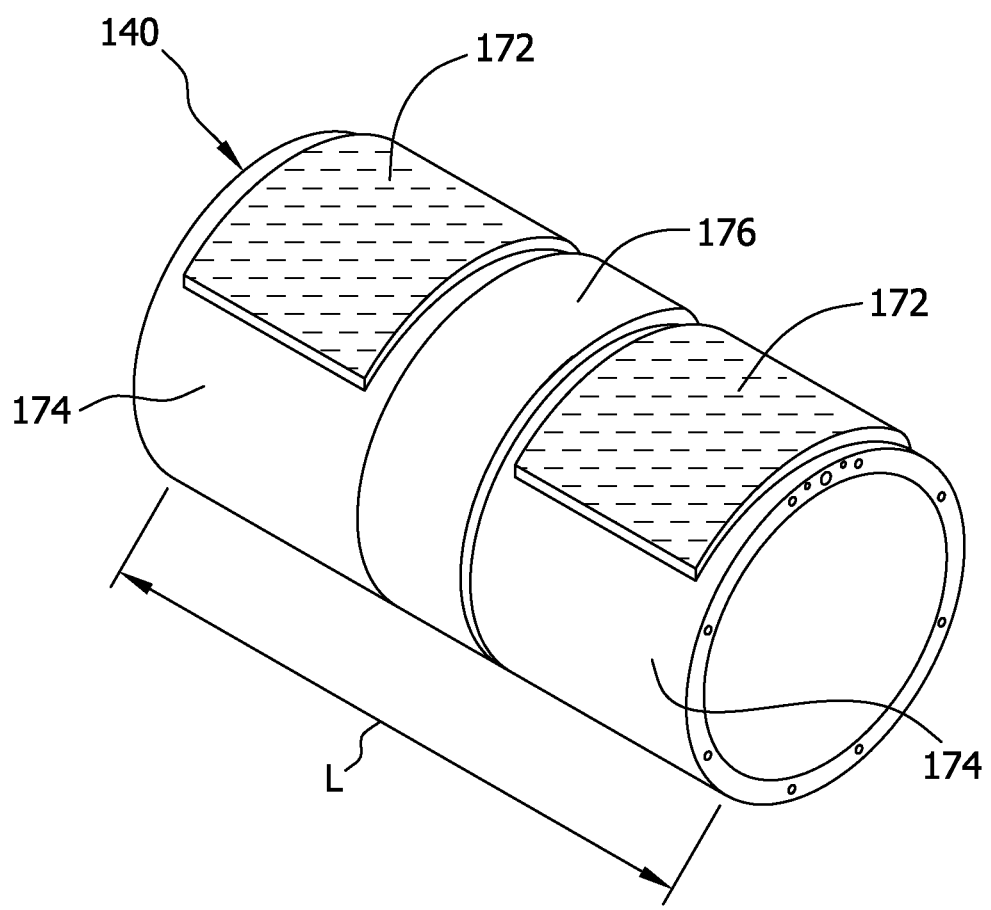
FIG. 9 is a perspective of a roller of the web treatment apparatus of FIG. 8 removed therefrom.

FIGS. 8 and 9 illustrate one suitable embodiment of the web treatment apparatus 106 for deadening or otherwise treating (e.g., embossing, cutting, bonding, aperturing) one or more webs as the webs pass through the apparatus. As explained above, the illustrated web treatment apparatus 106 is configured to deaden a portion of two webs (e.g., webs 102 of elastomeric laminate as illustrated FIG. 7) being moved generally parallel to each other through the apparatus. It is understood, however, that the apparatus can be configured to treat more or fewer than two webs. It is also understood that the webs do not need to be generally parallel to each other when they enter the web treatment apparatus 106. It is further understood that any suitable webs can be treated using the apparatus 106.

As seen in FIG. 8, the apparatus 106 includes a support frame, indicated generally at 120, supporting first and second rollers. The first roller is indicated generally by 140 and the second roller is indicated generally by 160. In the illustrated embodiment, the support frame 120 includes a back plate 122 and a base plate 124 extending generally perpendicular to the back plate. The back plate 122, which is generally rectangular, includes an elongate slot 126 for allowing webs to pass through the back plate. The slot 126 in the back plate 124 can have any suitable length and height to accommodate webs having various widths and thicknesses. It is contemplated that the back plate 122 can comprise two or more discrete, spaced-apart segments configured for allowing the webs to pass between the segments. As a result, the web or webs can extend outward beyond the first and second rollers 140, 160 as the web(s) is passing through the apparatus 106.

A pair of first brackets 130 is mounted on and extends outward from the back plate 122 for supporting the first roller 140 at a location adjacent to the slot 126. The first brackets 130 are sufficiently spaced apart and configured so that the first roller 140 can be located therebetween and supported by the brackets such that the first roller can rotate relative to the brackets. In the illustrated embodiment, a bottom edge of each of the first brackets 130 is generally aligned with an upper edge of the slot 126 in the back plate 122 but it is contemplated that the brackets can be spaced from the slot.

A pair of second brackets 132 is mounted to both the back plate 122 and the base plate 124 adjacent the intersection of the back plate with the base plate for supporting the second roller 160. The second brackets 132 are sufficiently spaced apart so that the second roller 160 can be located therebetween and supported by the brackets such that the second roller can rotate relative to the brackets. Each of the second brackets 132 comprises a generally U-shaped support member 134 and a generally rectangular and, more specifically, a square support element 136 slidingly received within the support member. The support elements 136, which receive the second roller 160, can be selectively moved with respect to the support members 134 to adjust (i.e., increase or decrease) the spacing and/or pressure between the first and second rollers 140, 160.

The spacing between the first and second rollers 140, 160 defines a nip, indicated generally 170. Thus, the nip 170 pressure and spacing can be adjusted by moving the second roller 160 either upward or downward with respect to the first roller 140. While the first roller 140 is fixedly mounted relative to the second roller 160 in the illustrated embodiment, it is contemplated that the first roller 140 can be moveably mounted relative to the second roller. In such an embodiment, the second roller 160 can be fixedly mounted or moveably mounted relative to the first roller 140. Accordingly, it is contemplated that both the first and second rollers 140, 160 can be moveably mounted to adjust the spacing and/or pressure at the nip 170.

A pair of third brackets 138 is mounted on the back plate 122 above the first roller 140. A generally square plate 142 is support by and extends between the third brackets. The third brackets 138 and square plate 140 cooperatively support a cam follower 144 (broadly, a "first pressure applicator"). The cam follower 144 is aligned generally with the center (i.e., the transverse axis) of the first roller 140. The cam follower 144 is in direct contact with an outer surface of the first roller 140 and operatively connected to a load source (not shown) for selectively applying a load or pressure to the first roller.

Another cam follower 146 (broadly, a "second pressure applicator") is disposed adjacent the base plate 124 and in direct contact with the center (i.e., the transverse axis) of the second roller 160. This cam follower 146 is in direct contact with an outer surface of the second roller 160 and operatively connected to a load source (not shown) for selectively applying a load or pressure to the second roller. It is understood that the cam followers 144, 146 can be operatively connected to the same load source or different load sources. In one suitable embodiment, each of the cam followers 144, 146 is operatively connected to separate, independently controlled load sources.

In the illustrated embodiment, the first roller 140 is a pattern roll and the second roller 160 is an anvil roll. It is contemplated, however, that the second roller 160 can be the pattern roll and the first roller 140 can be the anvil roll. It is also contemplated that both the first and second rollers 140, 160 can be pattern rolls.

As seen in FIG. 9, the first roller 140 can be, for example, a rigid steel roll with two generally rectangular raised areas 172 (broadly, "treatment areas") that are surrounded by smooth land areas 174 on its outer surface. The first roller 140 has two ends and a length L extending between the two ends. The raised areas 172 are raised above the surface of the land areas 174 by a height such that the pressure in the nip 170 between the bonding areas 172 and second roller 160 will be sufficient to treat the web. For example, in certain embodiments, nip pressures of at least about 500 pounds per lineal inch, more particularly at least about 600 pounds per lineal inch, and most particularly at least about 800 pounds per lineal inch can be achieved at the nip 170.

As illustrated in FIG. 9, a bearer ring 176 extends around the entire circumference of the first roller 160 and is aligned with the center of the roller. In one suitable embodiment, the bearer ring 176 has a height that is generally equal to or greater than the height of the raised areas 172. That is, the bearer ring 176 is raised above the surface of the land areas 174 by an amount generally equal to or greater than the raised areas 172. It is contemplated, however, that the bearer ring 176 can have a height that is less than the height of the raised areas 172. That is, the raised areas 172 can have a height greater than the height of the bearer ring 176.

As the first roller 140 and the second roller 160 rotate in opposite directions relative to each other, the bearer ring 176 contacts the second roller. With reference again to FIG. 8, the cam follower 144 directly contacts and applies a downward pressure to first roller 140 via the bearer ring 176. Thus, the bearer ring 176 contacts the second roller 160 with a predetermined pressure (e.g., between about 500 pounds per linear inch and about 800 pounds per linear inch).

Each of the raised areas 172 of the illustrated first roller 140 are disposed on opposite sides of the bearer ring 176 (FIGS. 8 and 9). That is, one of the raised areas 172 is located on one side of the bearer ring 176 (to the right as viewed in FIG. 9) and the other raised area is located on the other side of the bearer ring (to the left as viewed in FIG. 9). The illustrated embodiment of the first roller 140 has two raised areas but it is understood that the first roller could have more or fewer (i.e., one) raised area.

In the illustrated embodiment, each of the raised areas 172 comprises a pattern suitable for embossing and thereby deadening a portion of two webs as the webs pass through the apparatus 106. The raised areas 172 of the illustrated first roller 140 have substantially the same pattern. It is contemplated, however, that the patterns can be different. It is also contemplated that that the raised areas 172 can be configured to treat the webs differently. That is, for example, one of the raised areas 172 can be configured to emboss the web while the other web can be configured to bond the web.

With reference again to FIG. 8, the first roller 140 includes a suitable drive mechanism 178 comprising a shaft operatively connected to a suitable drive source (not shown) for rotating the first roller via the shaft in a first direction (indicated by arrow 180). Suitable drive sources include, for example, servo motors, camboxes. In the illustrated embodiment, the first direction 180 is counterclockwise but it understood that the first roller can be rotated in the clockwise direction.

The circumference of the illustrated first roller 140 is generally equal to the transverse width of the absorbent article 20 and the first roller is rotated by the drive source such that its surface speed generally matches the line speed of the web. As a result, every revolution of the first roller 140 corresponds to one absorbent article 20. It is contemplated, however, that the first roller 140 can have larger circumferences such that each revolution of the first roller corresponds to more than one absorbent article 20.

As mentioned above, the second roller 160 is an anvil roll (e.g., a smooth, hardened steel roll). It is contemplated, however, that the second roller 160 can be any suitable roll. For example, the second roller 160 can be a steel pattern roll having a pattern configured to mate with the pattern of the first roller 140. In another example, the second roller 160 can be a rubber coated roll.

One of the cam followers 146 directly contacts and applies an upward pressure sufficient to prevent roll deflection, which would detract from the desired level of treatment. In the illustrated embodiment, the upward pressure applied to the second roller 160 by the cam follower 146 is generally equal to and opposite to the downward pressure applied to the bearer ring 176 of the first roller 140 by the other cam follower 144. It is contemplated that the predetermined pressures applied by the cam followers 144, 146 can be different. That is, the upward pressure applied to the second roller 160 by the cam follower 146 can be other than equal to the downward pressure applied to the bearer ring 176 of the first roller 140 by the other cam follower 144. It is also contemplated that one of the two cam followers can be omitted such that pressure is applied to either the first roller 140 via the bearer ring 176 or to the second roller 160.

The second roller 160 includes a suitable drive mechanism 182 comprising a shaft operatively connected to a suitable drive source (not shown) for rotating the first roller via the shaft in a second direction (indicated by arrow 184), which is opposite to the first direction 180 of the first roller 140. Suitable drive sources include, for example, servo motors, camboxes. In the illustrated embodiment, the second direction 184 is clockwise but it understood that the second roller 160 can be rotated in the counterclockwise direction, such as, when the first roller 140 is rotated in the clockwise direction.

The circumference of the illustrated second roller 160 is generally equal to the circumference of the illustrated first roller 140. It is understood, however, that the second roller 160 can have any suitable circumference. That is, the second roller 160 can have a circumference that is greater than or less than the circumference of the first roller 140.

In one suitable embodiment, at least one of the first and second rollers 140, 160 is heated to a predetermined temperature that is above ambient during use. The heat and pressure applied to the webs by the raised areas 172 of there first roller 140 as they pass through the nip 170 are sufficient to cause portions of the elastomeric laminate to deaden or otherwise be treated. The specific desired temperature is dependent upon various parameters including, for example, the composition of the webs and the residence time of the webs in the nip 170. The residence time of the webs within the nip 170 is dependent on line speed (i.e., how fast the web is traveling) as well as roll diameters.

In one embodiment, the temperature at the nip 170 can be between about 180 degrees Fahrenheit and about 490 degrees Fahrenheit. In one suitable embodiment, both the first roller 140 and the second roller 160 can be heated to the same or different temperatures either simultaneously or alternatively. In another suitable embodiment, only one of the first and second rollers 140, 160 can be heated. It is also contemplated that in some embodiments, the nip 170 can be at ambient temperature during use. In such an embodiment, neither the first nor the second roller 140, 160 need to be capable of heating.

It has been found that higher nip pressures can be used in the present apparatus 106. In the apparatus 106 seen in FIG. 8, for example, nip pressures between 500 pounds per linear inch and about 800 pounds per linear inch can be achieved. It is contemplated that the nip pressures can be greater than 800 pounds per linear inch or less than 500 pounds per linear inch without departing from some aspect of this invention.

Figure 10:
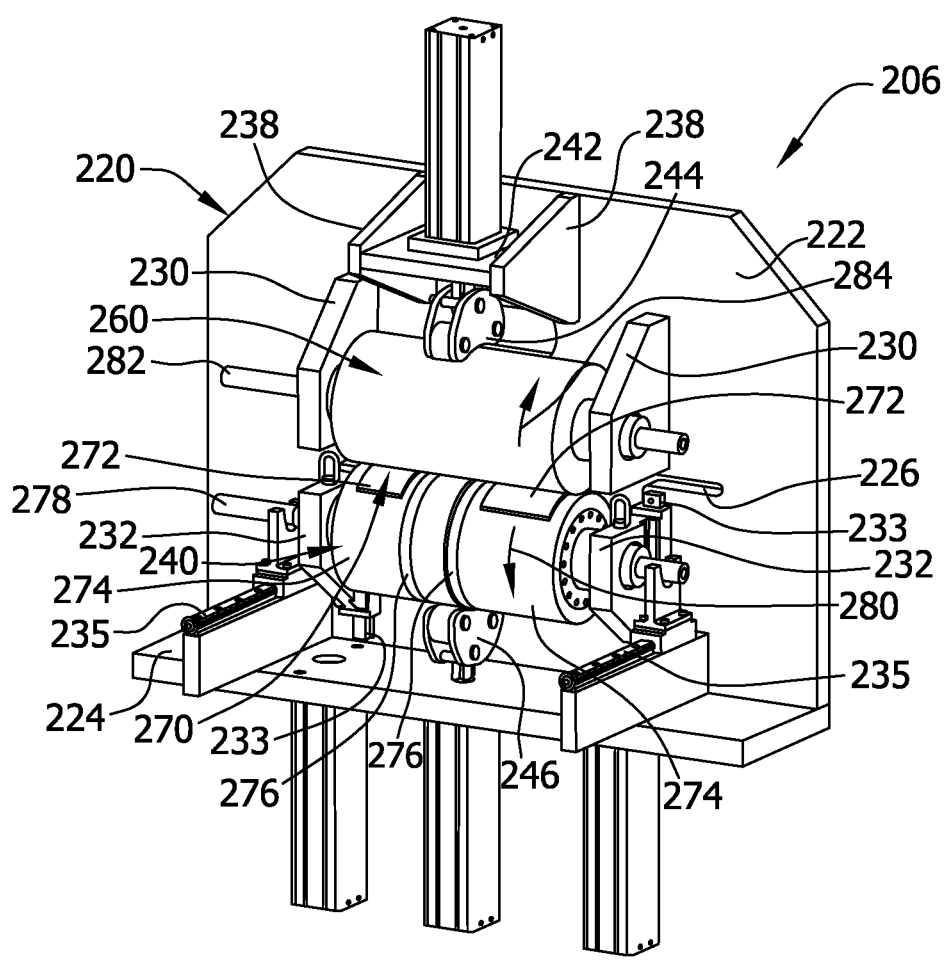
FIG. 10 is a perspective view of another embodiment of a web treatment apparatus.

FIG. 10 illustrates another suitable embodiment of a web treatment apparatus, indicated generally at 206, for deadening or otherwise treating (i.e., embossing, cutting, bonding, aperturing) one or more webs. The illustrated web treatment apparatus 206 is configured to deaden a portion of two webs (e.g., webs 102 of elastomeric laminate as illustrated FIG. 7) being moved generally parallel to each other through the apparatus. It is understood, however, that the apparatus can be configured to treat more or fewer than two webs. It is also understood that the webs do not need to be generally parallel to each other when they enter the web treatment apparatus 206. It is further understood that any suitable webs can be treated using the apparatus 206.

As seen in FIG. 10, the apparatus 206 includes a support frame, indicated generally at 220, supporting first and second rollers. The first roller is indicated generally by 240 and the second roller is indicated generally by 260. In this embodiment, the first roller 240 is located beneath the second roller 260, which is the opposite the orientation of the embodiment illustrated in FIGS. 8 and 9 wherein the first roller 140 was located above the second roller 160. It is understood that the first and second rollers can have any suitable alignment (e.g., side-by-side).

In the illustrated embodiment, the support frame 220 includes a back plate 222 and a base plate 224 extending generally perpendicular to the back plate. The back plate 222, which is generally rectangular, includes an elongate slot 226 for allowing webs to pass through the back plate. The slot 226 in the back plate 224 can have any suitable length and height to accommodate webs having various widths and thicknesses. It is contemplated that the back plate 222 can comprise two or more discrete, spaced-apart segments configured for allowing the webs to pass between the segments.

A pair of first brackets 230 is mounted on and extends outward from the back plate 222 for supporting the second roller 260 at a location adjacent to the slot 220. The first brackets 230 are sufficiently spaced apart and configured so that the second roller 260 can be located therebetween and supported by the brackets such that the second roller can rotate relative to the brackets. In the illustrated embodiment, a bottom edge of each of the first brackets 230 is generally aligned with an upper edge of the slot 226 in the back plate 222 but it is contemplated that the brackets can be spaced from the slot.

A pair of second brackets 232 is mounted on runners 233 secured to the back plate 222 and runners 235 secured to the base plate 224 adjacent the intersection of the back plate with the base plate for supporting the first roller 240. The second brackets 232 are sufficiently spaced apart so that the first roller 260 can be located therebetween and supported by the brackets such that the first roller can rotate relative to the brackets. Each of the second brackets 232 and, thus the first roller 240, is moveable in a vertical direction (i.e., up and down) along the runners 233 secured to the back plate 222 and in a horizontal direction (i.e., forward and backward) along the runners 235 secured to the base plate 224. As a result, the first roller 240 can be moved toward and away from both the back plate 222 and the base plate 224.

Accordingly, the first roller 240 can be selectively moved relative to the second roller 260 to adjust (i.e., increase or decrease) the spacing and/or pressure between the first and second rollers 240, 260. The spacing between the first and second rollers 240, 260 defines a nip, indicated generally 270. Thus, the nip 20 pressure and spacing can be adjusted by moving the first roller 240 with respect to the second roller 260. While the second roller 260 is fixedly mounted relative to the first roller 240 in this embodiment, it is contemplated that the second roller can be moveably mounted relative to the first roller. In such an embodiment, the first roller 240 can be fixedly mounted or moveably mounted relative to the second roller 260. Accordingly, it is contemplated that both the first and second rollers 240, 260 can be moveably mounted to adjust the spacing and/or pressure at the nip 270.

A pair of third brackets 238 is mounted on the back plate 222 above the second roller 260. A generally square plate 242 is support by and extends between the third brackets 238. The third brackets 238 and square plate 242 cooperatively support a cam follower 244. The cam follower 244 is aligned generally with the center (i.e., the transverse axis) of the second roller 260. The cam follower 244 is in direct contact with an outer surface of the second roller 260 and operatively connected to a load source for selectively applying a load or pressure to the second roller.

Another cam follower 246 is disposed adjacent the base plate 224 and in direct contact with the center (i.e., the transverse axis) of the first roller 240. This cam follower 246 is in direct contact with an outer surface of the first roller 240 and operatively connected to a load source for selectively applying a load or pressure to the first roller. It is understood that the cam followers 244, 246 can be operatively connected to the same load source or different load sources. In one suitable embodiment, each of the cam followers 244, 246 is operatively connected to separate, independently controlled load sources.

In the illustrated embodiment, the first roller 240 is a pattern roll and the second roller 260 is an anvil roll. It is contemplated, however, that the second roller 260 can be the pattern roll and the first roller 240 can be the anvil roll. It is also contemplated that both the first and second rollers 240, 260 can be pattern rolls.

As seen in FIG. 10, the first roller 240 can be, for example, a rigid steel roll with two generally rectangular raised areas 272 that are surrounded by smooth land areas 274 on its outer surface. The raised areas 272 are raised above the surface of the land areas 274 by a height such that the pressure in the nip 270 between the raised areas 272 and second roller 260 will be sufficient to treat the web.

A pair of spaced-apart, bearer rings 276 extends around the entire circumference of the first roller 240 and is aligned with but not located in the center of the roller. In other words, the bearer ring 276 extends around portions of the first roller 240 that are equidistant from the center of the first roller. That is, each of the bearer rings 276 is spaced from the center of the first roller 240 by the same distance. Each of the bearer rings 276 has a height that is equal to or greater than the height of the raised areas 272. That is, the bearer rings 276 are raised above the surface of the land areas 274 by an amount equal to or greater than the raised areas 272. Thus, as the first roller 240 and the second roller 260 rotate in opposite directions relative to each other, the bearer rings 276 contact the second roller.

Moreover, the cam follower 246 directly contacts and applies an upward pressure to the first roller 240 thereby causing the bearer rings 276 to apply approximately the same pressure to the second roller 260. Thus, the bearer rings 276 contact the second roller 260 with a predetermined pressure (e.g., between about 500 pounds per linear inch and about 800 pounds per linear inch).

Each of the raised areas 272 are disposed outwardly from and on opposite sides of the bearer rings 276. That is, one of the raised areas 272 is located on one side of the bearer rings 276 (to the right as viewed in FIG. 10) and the other raised area is located on the other side of the bearer ring (to the left as viewed in FIG. 10). The illustrated embodiment of the first roller 240 has two raised areas but it is understood that the first roller could have more or fewer (i.e., one) raised area.

In the illustrated embodiment, each of the raised areas 272 comprises a pattern suitable for embossing and thereby deadening a portion of two webs as the webs pass through the apparatus 206. In the illustrated, the raised areas 272 have substantially the same pattern. It is contemplated, however, that the patterns can be different. It is also contemplated that that the raised areas 272 can be configured to treat the webs differently. That is, for example, one of the raised areas 272 can be configured to emboss the web while the other web can be configured to bond the web.

With reference still to FIG. 10, the first roller 240 includes a suitable drive mechanism 278 including a shaft operatively connected to a suitable drive source (not shown) for rotating the first roller via the shaft in a first direction (indicated by arrow 280). Suitable drive sources include, for example, servo motors, camboxes. In the illustrated embodiment, the first direction 280 is counterclockwise but it understood that the first roller can be rotated in the clockwise direction.

The circumference of the illustrated first roller 240 is generally equal to the transverse width of the absorbent article 20 and the first roller is rotated by the drive source such that its surface speed generally matches the line speed of the web. As a result, every revolution of the first roller 240 corresponds to one absorbent article 20. It is contemplated that the first roller 240 can have larger circumferences such that each revolution of the first roller corresponds to more than one absorbent article 20.

As mentioned above, the second roller 260 is an anvil roll (e.g., a smooth, hardened steel roll). It is contemplated, however, that the second roller 260 can be any suitable roll. For example, the second roller 260 can be a steel pattern roll having a pattern configured to mate with the pattern of the first roller 240. In another example, the second roller 260 can be a rubber coated roll.

One of the cam followers 244 directly contacts and applies a downward pressure to the second roller 260 generally at the center thereof to inhibit deflection of the second roll. In the illustrated embodiment, the downward pressure applied to the second roller 260 by the cam follower 244 is generally equal to and opposite to the upward pressure applied to the first roller 240 by the other cam follower 246. It is contemplated that the predetermined pressures applied by the cam followers 244, 246 can be different. That is, the upward pressure applied to the second roller 260 by the cam follower 244 can be other than equal to the downward pressure applied to the first roller 240 by the other cam follower 246. It is also contemplated that one of the two cam followers 244, 246 can be omitted such that pressure is applied to only the first roller 240 or to the second roller 260.

As seen in FIG. 10, the second roller 260 includes a suitable drive mechanism 282 including a shaft operatively connected to a suitable drive source (not shown) for rotating the first roller via the shaft in a second direction (indicated by arrow 284), which is opposite to the first direction 280 of the first roller 240. Suitable drive sources include, for example, servo motors, camboxes. In the illustrated embodiment, the second direction 284 is clockwise but it understood that the second roller 260 can be rotated in the counterclockwise direction, such as, when the first roller 240 is rotated in the clockwise direction.

The circumference of the illustrated second roller 260 is generally equal to the circumference of the illustrated first roller 240. It is understood, however, that the second roller 260 can have any suitable diameter. That is, the second roller 260 can a circumference that is greater than or less than the circumference of the first roller 240.

In one suitable embodiment, at least one of the first and second rollers 240, 260 is heated to a predetermined temperature that is above ambient during use. The heat and pressure applied to the webs by the raised areas 272 of there first roller 240 as they pass through the nip 270 are sufficient to cause portions of the web to be treated (e.g., to deaden portions of the webs of elastomeric laminate seen in FIG. 7). The specific desired temperature is dependent upon various parameters including, for example, the composition of the webs and the residence time of the webs in the nip 270. The residence time of the webs within the nip 270 is dependent on line speed (i.e., how fast the web is traveling) as well as roll diameters.

In one embodiment, the temperature at the nip 270 can be between about 180 degrees Fahrenheit and about 490 degrees Fahrenheit. In one suitable embodiment, both the first roller 240 and the second roller 260 can be heated to the same or different temperatures simultaneously or alternatively. In another suitable embodiment, only one of the first and second rollers 240, 260 can be heated. It is also contemplated that in some embodiments the nip 270 can be at ambient temperature during use. In such an embodiment, neither the first nor the second roller 240, 260 need to be capable of heating.

It has been found that higher nip pressures can be used in the present apparatus 206. In the apparatus 206 seen in FIG. 10, for example, nip pressures between 500 pounds per linear inch and about 800 pounds per linear inch can be achieved. It is contemplated that the nip pressures can be greater than 800 pounds per linear inch or less than 500 pounds per linear inch without departing from some aspect of this invention.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for treating at least one web passing through the apparatus, the apparatus comprising:
    a first roller having a pair of spaced apart ends, a length extending between the ends, a circumference, and at least one bearer ring extending around the circumference of the first roller generally at a center of the first roller;
    a first pressure applicator in direct contact with the at least one bearer ring and operatively connected to a load source for selectively applying a load to the at least one bearer ring; and
    a second roller positioned adjacent the first roller to define a nip for receiving the at least one web.

2. The apparatus as set forth in claim 1 wherein the first roller further comprises at least one treatment area adapted to treat the at least one web passing through the apparatus.

3. The apparatus as set forth in claim 2 wherein the first roller comprises two treatment areas adapted to treat the at least one web passing through the apparatus.

4. The apparatus as set forth in claim 3 wherein the two treatment areas are located on opposite sides of the bearer ring.

5. The apparatus as set forth in claim 2 wherein the at least one treatment area is adapted to emboss a portion of the web as it passes through the apparatus.

6. The apparatus as set forth in claim 1 wherein the first pressure applicator comprises a cam follower.

7. The apparatus as set forth in claim 1 further comprising a second pressure applicator adapted to apply a load to the second roller, the load applied to the second roller by the second pressure applicator being generally aligned with and opposite the force applied to the first roller by the first pressure applicator.

8. The apparatus as set forth in claim 1 wherein at least one of the first and second rollers is capable of being heated.

9. Apparatus for treating at least one web comprising:
    a first roller having a pair of spaced apart ends, a length extending between the ends, a circumference, and at least one bearer ring extending around the circumference of the first roller, the at least one bearer ring being disposed between and spaced from the ends of the first roller,
    a pressure applicator in direct contact with the at least one bearer ring and operatively connected to a load source for selectively applying a load to the at least one bearer ring; and
    a second roller positioned adjacent the first roller to define a nip for receiving the at least one web.

10. The apparatus as set forth in claim 9 wherein the at least one bearer ring comprises a single bearer ring located generally at a center of the first roller.

11. The apparatus as set forth in claim 9 wherein the at least one bearer ring comprises two bearer rings, each of the bearer rings being spaced equidistant from a center of the first roller.

12. The apparatus as set forth in claim 9 wherein the first roller comprises at least one treatment area.

13. The apparatus as set forth in claim 12 wherein the at least one treatment area comprises two treatment areas, one of the two treatment areas being located between the at least one bearer ring and one of the ends of the first roller and the other treatment area of the two treatment areas being located between the at least one bearer ring and the other end of the first roller.

14. The apparatus as set forth in claim 12 wherein the at least one bearer ring and the at least one treatment area have substantially the same height.

15. The apparatus as set forth in claim 9 wherein the pressure applicator comprises a cam follower.

16. The apparatus as set forth in claim 9 further comprising a support frame for supporting the first and second rollers relative to each other.

17. The apparatus as set forth in claim 16 wherein the support frame is configured for allowing at least one of the first and second rollers to be moved relative to the other roller.

18. Apparatus for treating at least one web comprising:
    a first roller having a pair of spaced apart ends, a length extending between the ends, a circumference, and at least one bearer ring extending around the circumference of the first roller, the at least one bearer ring being disposed between and spaced from the ends of the first roller;
    a second roller positioned adjacent the first roller to define a nip for receiving the at least one web;
    a support frame for supporting the first and second rollers relative to each other, the support frame being configured for allowing at least one of the first and second rollers to be moved relative to the other roller; and
    a pressure applicator in direct contact with at least one of the first roller and the second roller, the pressure applicator being operatively connected to a load source for selectively applying a load to the at least one of the first roller and the second roller.

19. The apparatus as set forth in claim 18 wherein the pressure application is in direct contact with the at least one bearer ring of the first roller.

20. The apparatus as set forth in claim 18 wherein the pressure applicator is a cam follower.

* * * * *